United States Patent [19]

Nelson et al.

[11] Patent Number: 4,689,304
[45] Date of Patent: Aug. 25, 1987

[54] AIR/LIQUID DETECTION DEVICE FOR BLOOD SAMPLE ANALYSIS

[75] Inventors: Robert J. Nelson, North Chicago, Ill.; Dean M. Ball, Gainesville, Ga.

[73] Assignee: Abbott Laboratories, North Chicago, Ill.

[21] Appl. No.: 663,256

[22] Filed: Oct. 19, 1984

[51] Int. Cl.⁴ .................................... G01N 21/43
[52] U.S. Cl. ........................... 435/291; 435/808; 356/39; 356/436; 356/134
[58] Field of Search ............... 435/808, 291; 356/39, 356/40, 41, 42, 436, 409, 414, 134

[56] References Cited

U.S. PATENT DOCUMENTS 3,636,360 1/1972 Oishi ..................... 356/134 X
4,381,895 5/1983 Hughes ..................... 356/134
4,573,796 3/1986 Martin ..................... 356/39 X Primary Examiner—Alan Cohan
Attorney, Agent, or Firm—Martin L. Katz; James L. Wilcox

[57] ABSTRACT

An air/fluid sensing device useful in apparatus for analyzing biological material. The device includes one or more light sources directed at a surface of a container defining an interface with the space enclosed thereby. Depending on whether fluid is present in or absent from the container at the location where said one or more light sources are directed to said surface, the light emanating from the sources will be refracted or reflected, thereby giving an indication of whether fluid is present or absent at said locations.

20 Claims, 7 Drawing Figures

AIR/LIQUID DETECTION DEVICE FOR BLOOD SAMPLE ANALYSIS

BACKGROUND OF THE INVENTION

This invention generally relates to apparatus and methods for analyzing a biological material to ascertain whether a particular substance is present or absent. More particularly, this invention relates to such apparatus and methods wherein the biological material is preferably human blood serum and the substance whose presence or absence is to be determined is preferably a composition indicative of disease, commonly referred to as an antigen. For example, in one aspect of this invention, human blood serum is analyzed to determine whether a hepatitis B surface antigen is present or absent.

Apparatus and methods for analyzing blood serum to ascertain whether a disease is present are especially important in situations where blood is donated by members of the public for the purpose of being subsequently administered to others by transfusion. In such cases it is necessary to analyze the donated blood to ensure that it is free from disease, lest the future user unknowingly contract that disease as a result of such transfusion. The disease for which analysis is most frequently conducted is hepatitis, though other diseases, including AIDS, may also be the subject of such analysis. Thus, though the descriptions referred to herein may specifically refer to hepatitis, it should be understood that such disease is exemplary rather than limitative, the scope of the invention being defined by the appended claims.

In one desirable apparatus for analyzing blood serum for substances indicative of disease, a rotatable incubation wheel is provided for moving a multiplicity of blood serum-containing cartridges to a plurality of operating stations. Such cartridges typically include a plunger, longitudinally movable through a cylindrical cavity containing the blood sample to be analyzed. A polystyrene bead, coated with a disease specific antibody or antigen, is ordinarily placed inside the cylindrical cavity of the cartridge, where it can be contacted by a quantity of blood serum subsequently placed therein. As explained hereinafter, as the multiplicity of cartridges are moved by the incubation wheel through the various operating stations, various substances are introduced into the cartridge cavity where they are brought into contact with the antibody-coated or antigen-coated polystyrene bead. Depending on the nature of the substances so introduced, and whether the blood serum contains a substance characteristic of the disease that is the object of the analysis then being undertaken, the contents of the cavity may be assayed to provide a "positive" or "negative" indication of that disease.

Though blood analyzing apparatus and methods of the type described have been successfully employed, they are not without certain drawbacks and deficiencies. Accordingly, it is a primary object of this invention to provide improved apparatus and methods useful in conjunction with apparatus for determining whether a particular quantity of blood serum is characterized by a substance indicative of a particular disease. It is another object of the invention to accomplish the foregoing, at least in part, by providing an air/liquid sensing device which helps ensure that liquid necessary for conducting the analysis has indeed been passed from a liquid reservoir to the cartridge containing the coated bead. It is yet another object of this invention to provide such a air/liquid sensing device which accomplishes these results in a reliable, hands-free operation.

SUMMARY OF THE INVENTION

The foregoing objects of the invention, along with numerous features and advantages, are achieved in an apparatus for analyzing a biological material by applying a fluid, normally a liquid, to a coated bead carried inside a cartridge. The apparatus includes a device for detecting the presence or absence of such fluid prior to its application to the cartridge comprising a fluid container, communicating with the cartridge, having a surface defining an interface with the space enclosed by the container. A light source is adapted to apply an incident ray to the surface of the container such that a component of the ray is reflected along a predetermined path when fluid is absent from the container. A light responsive element, disposed along the predetermined path is adapted to produce a signal upon receipt of the reflected component. This signal is indicative of the absence of fluid in the container.

According to an alternative embodiment of the invention, a plurality of light sources are provided to apply incident rays to the surface of the container at a plurality of spaced locations on the surface. A component of each of the rays will be reflected along a predetermined path when fluid is absent from the container at the particular location where the incident ray was applied to the container surface. A light responsive element is disposed along each of the predetermined paths and each will produce a signal upon receipt of the component reflected along its path. The signals are indicative of the volume of fluid present in the container.

In another aspect of the invention there is provided a method for detecting the presence or absence of or the volume of fluid present, prior to and following its application to a cartridge containing a coated bead. The method includes the steps of providing a container having a surface defining an interface with the space enclosed by the container, applying one or more incident rays to the surface at angles equal to or greater than the critical angle for an air/container interface but less than the critical angle for a fluid/container interface, and reflecting a component of each of the rays from the air/container interface, the reflected components being indicative of the absence of fluid in the container, or of the volume of fluid present in the container.

BRIEF DESCRIPTION OF THE DRAWINGS

Exemplary embodiments of the invention summarized above are shown in the accompanying drawings wherein.

DETAILED DESCRIPTION OF EXEMPLARY EMBODIMENTS OF THE INVENTION

As explained hereinbefore, the present invention pertains to apparatus and methods for analyzing biological material to determine whether a particular substance is present or absent. In a preferred form of the invention, the biological material to be analyzed is human blood serum, and the substance whose presence or absence is to be determined is a composition associated with the blood serum indicative of disease. Such composition usually contains a protein or carbohydrate which, when introduced into the body, stimulates the production of an antibody. The specific protein or carbohydrate which incites antibody production is commonly referred to as an antigen.

For exemplary purposes only, the detailed description that follows explains the apparatus and methods in terms of analyzing a quantity of human blood serum for purposes of determining whether that blood serum has a substance indicative of hepatitis, i.e., the blood serum is analyzed to determine whether an antigen corresponding to surface B hepatitis is present. It should be clearly understood, however, that the present invention is not so limited, but is also useful in analyzing blood serum to determine whether other substances, indicative of other diseases, may be present, in analyzing biological fluids such as saliva, urine, throat swabs and the like, or in other applications not specifically described.

Figure 1:
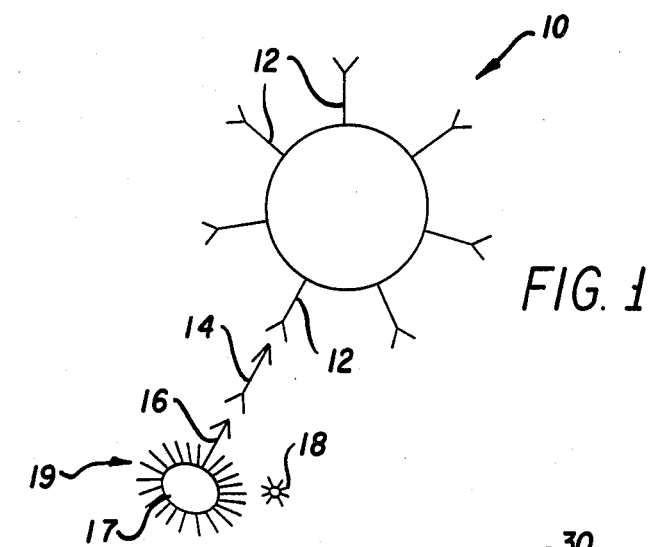
FIG. 1 is a schematic representation of a bead, and the various substances adhering thereto, preferably used in connection with carrying out the present invention.

The present invention is preferably carried out by using means to which various substances are applied for purposes of conducting an analysis of a biological material such as human blood serum. As shown in FIG. 1, such means preferably take the form of a small bead 10, typically formed from polystyrene or some similar material, and typically being on the order of about ¼ inch in diameter. In accordance with well-known procedures, bead 10 is coated with an antibody specific to the particular disease that will be the subject of analysis. If this disease is hepatitis, for example, bead 10 will be coated with a antibody 12 to hepatitis B surface antigen 14, represented diagrammatically by a plurality of inverted arrows, disposed about the periphery of bead 10. If another disease, such as AIDS, is the subject of analysis, bead 10 will, of course, be coated with a different antibody or AIDS specific agent.

In accordance with well-known and well-understood biological phenomenon which need not be described herein, an antibody for a particular disease will bond to the antigen corresponding to that disease when the antibody and the antigen are brought into contact under suitable conditions. Thus, if proper temperature and time parameters exist, a hepatitis B surface antigen 14, brough into contact with the antibody 12 to hepatitis B surface antigen 14 covering bead 10, will become bonded thereto. Similarly, an antibody 16 conjugated with an enzyme marker 17 to provide antibody enzyme conjugate 18, may become bonded to antigen 14 under proper time and temperature conditions. Antigen 14, and antibody-enzyme conjugate 19 are shown in diagrammatic form in FIG. 1.

Certain color-developing substances, commonly known as chromophores and represented diagrammatically at 18 in FIG. 1, are known to change color in the presence of certain materials. One such chromophore is tetramethylbenzidine. When the enzyme marker is horse radish peroxidase, tetramethylbenzidine in a mixture including perioxide can be used to provide an indication that the hepatitis B surface antigen is present. The presence of this particular antigen in the blood serum under analysis is, of course, indicative of a "positive" test for heptatitis.

Figure 2:
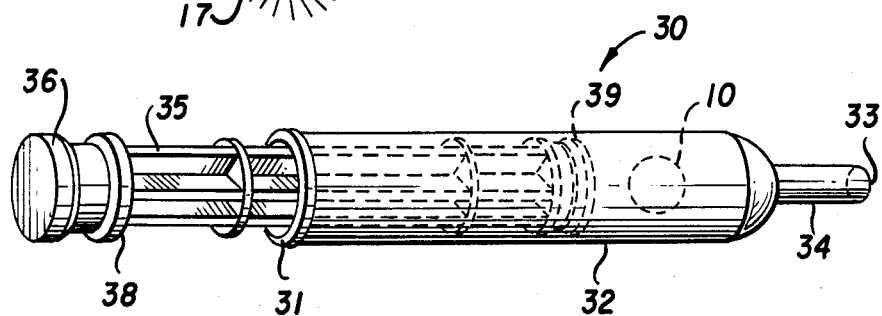
FIG. 2 is a schematic view of a cartridge containing the bead shown in FIG. 1, said cartridge being representative of the type used in connection with the present invention.

Bead 10, coated with appropriate antibody 12, is deposited in a laboratory cartridge 30 of the type shown in FIG. 2. Cartridge 30 has a body portion 37 defining a substantially cylindrical cavity 32 having a distal opening 31. At its proximal end body portion 37 tapers to a tip protein 34 terminating in a proximal opening 33. In this exemplary embodiment, bead 10, coated with antibody 12, is deposited in cavity 32 before analysis begins.

Cartridge 30 further includes a plunger 35 having a distal handle 36 formed with a flange 38 to assist in actuation of the plunger. Associated with plunger 35 is at least one sealing ring 39 which serves as a barrier to fluid in cavity 32, and which forces such fluid through tip 34 and out proximal opening 33 when plunger 35 is urged through cavity 32.

Initially, plunger 35 is retracted from cavity 32 so that bead 10, coated with antibody 12, can be put into cavity 32 via distal opening 31. Means (not shown) may then be used to draw a quantity of material, such as blood serum, into cavity 32 of cartridge 30, permitting that material to contact the antibody-coated bead 10. Alternatively, pipetting may be used so that the material to be analyzed will not enter cavity 32 until a timed operation is about to commence. This enables one to accurately control the time in which the material is in contact with the antibody 12 on bead 10.

Figure 3:
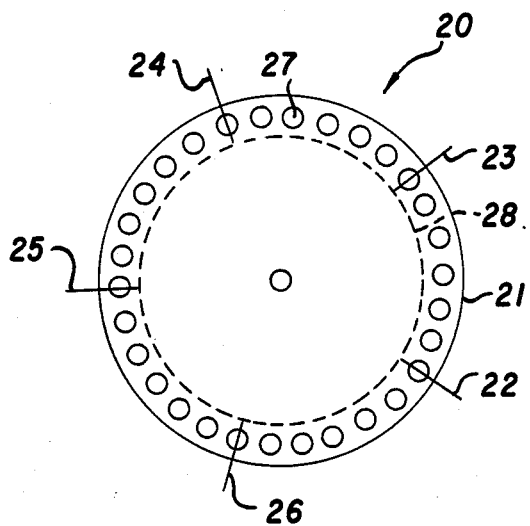
FIG. 3 is a very simplified schematic representation of apparatus of the type used in carrying out the present invention, said apparatus being adapted to carry a multiplicity of cartridges of the type shown in FIG. 2.

Cartridge 30, may then be loaded on an apparatus of the type represented schematically by apparatus 20 in FIG. 3. Apparatus 20 includes a rotating incubation wheel 21 having a plurality of cartridge receiving cavities 27 and an incubation heater strip schematically illustrated at 28. Apparatus 20 further includes a plurality of operating stations identified by reference numerals 22–26. Operating station 22 represents a load station where cartridges containing the material to be analyzed and the bead 10 are sequentially loaded onto wheel 21. For exemplary purposes, the material to be analyzed is referred to hereinafter as blood serum.

After cartridge 30 has been loaded into incubation wheel 21, and the blood serum is brought into contact with antibody-coated bead 10, wheel 21 is preferably rotated for approximately 37 minutes while subjecting cartridge 30 to temperatures of about 40° C. It has been found that these parameters of time and temperature represent a sufficient incubation period for any hepatitis B surface antigen associated with the blood serum in cavity 31 of cartridge 30 to bond to the antibody 12 coated on bead 10. Thus, if the blood serum in cartridge 30 is infected with hepatitis, hepatitis B surface antigen will be present, and it will become bonded to the heptatitis antibody coated head 10 after the incubation period has been concluded. On the other hand, if the blood serum in cartridge 30 is not infected with hepatitis, there will be no hepatitis B surface antigen present in the blood serum, and therefore no such antigen will be available for bonding to the antibody-coated surface of bead 10.

After cartridge 30 has been rotated by wheel 21 for a period of time sufficient to cause any hepatitis antigen associated with the blood serum contained in cavity 32 to become bonded to the antibody-coated surface of bead 10, the apparatus 20 causes wheel 21 to stop at operating station 23. At operating station 23, the excess blood serum is discharged from cavity 32, the cavity is washed, and then the contents, i.e., bead 10 with antibody 12 and antigen 14 successively bonded thereto, is exposed to an antibody-enzyme conjugate 19. In this exemplary embodiment enzyme marker 17 is a specific compound known as horse radish peroxidase. Being hepatitis specific, antibody 16, (and enzyme marker 17) bonds to antigen 14 for reasons previously explained. In summary, at operating station 23 the portion of the blood serum which did not bond to the antibody-coated bead 10 is first expelled from cavity 32, and the cavity is then washed to removed residue therein. When this washing operation is completed, the antibody enzyme conjugate 19 is introduced into cavity 32.

After antibody-enzyme conjugate 19 has been introduced into cavity 32, wheel 21 is again operated, causing cartridge 30 to be rotated for about 15 minutes at a temperature of approximately 40° C. until the reaction is complete. When this second incubation period is completed, wheel 21 stops at operating station 24 where another washing cycle is undertaken to remove all conjugate and enzyme material from cavity 32 which did not bond to the bead 10 during the second incubation process. When the unbonded material is removed, the color-developing chromophore mixture is introduced into cavity 32. This chromophore mixture preferably includes the chromophore tetramethylbenzidine mixed with peroxide. Tetramethylbenzidrine will turn blue in the presence of peroxide if the enzyme horse radish peroxidase is present. Of course, antibody-enzyme conjugate 19 is present only if bonded to antigen 14; and antigen 14 is present only if the blood serum originally introduced into the cartridge 30 was infected with hepatitis. If the blood serum was not so infected, there would have been no antigen 14 bonded to the antibody-coated bead 10, no conjugate bonded to the antigen 14, and therefore no enzyme 17 to cause chromophore 18 to change color. In short, the changing of chromophore 18 to a blue color is a "positive" indication that the blood serum originally deposited in cavity 32 of cartridge 30 was infected with hepatitis. As explained in greater detail hereinafter some of the functions performed at operation stations 23 and 24 are carried out with the use of an air/liquid sensing device such as shown in FIGS. 4-7.

After the chromophore 18 is introduced, the cartridge 30 is again rotated on wheel 21 for about eight minutes at approximately 40° C. When this final incubation period is completed, wheel 21 is stopped at operating station 25. It is at this operating station where a sample of the chorophore 18, representative of the blood serum originally deposited in cartridge 30, is ejected into a chamber and analyzed by an optical readout device. If the chromophore 18 turned blue as a result of the presence of enzyme 17, the optical readout device will develop a signal indicative of a "positive" hepatitis reaction. The absence of this signal, on the other hand, is indicative of a "negative" hepatitis reaction.

After the chromophore is ejected at operating station 25, and the optical analysis is undertaken, wheel 21 moves cartridge 30 to operating station 26. It is at operating station 26 that cartridge 30 is removed from wheel 21 of apparatus 20. It should be understood that throughout the course of this analysis, other cartridges may be simultaneously loaded, washed, and removed, whereby the results of numerous analyses can be completed during the time any single cartridge is loaded at operating station 22 and subsequently removed from apparatus 20 at operating station 26.

Figure 4:
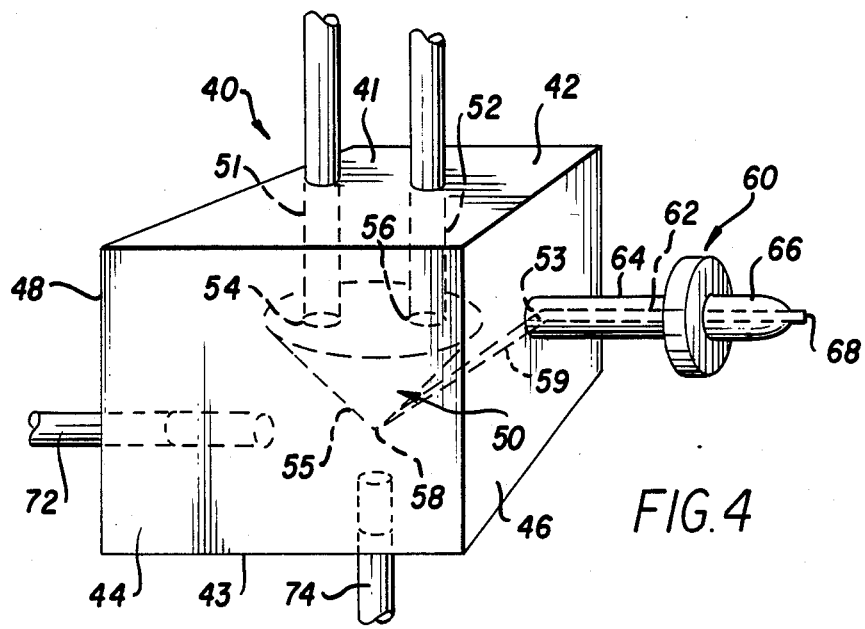
FIG. 4 is a simplified perspective view of an air/liquid sensing device used as part of the apparatus shown in FIG. 3, and being representative of one preferred embodiment of the present invention.

Referring now to FIG. 4 an exemplary embodiment of the air/liquid sensing device 40 is shown. Sensing device 40 is preferably formed from an acrylic block 41 having a top face 42, a bottom face 43, a front face 44 and a pair of opposite side faces 46, 48. Formed inside the acrylic block 41 of sensing device 40 is a cavity which serves as a container 50. Container 50 is preferably of substantially conical shape and is characterized by a surface 55 defining an interface with the space enclosed by container 50. Thus, when container 50 is filled with fluid, surface 55 defines an interface between the container material and the fluid, sometimes referred to herein as the container/fluid interface. On the other hand when fluid is absent from container 50, surface 55 defines an interface between the container material and the ambient air, sometimes referred to herein as the container/air interface.

A pair of inlet passages 51, 52 extends from top face 42 to the base of container 50, passages 51, 52 communicating, respectively, with container 50 via a pair of inlets 54, 56. At the apex of container 50 is an outlet 58. An outlet passage 59 extends from outlet 58 to side face 46 of block 41. Outlet passage 59 terminates in a port 53 which communicates with a valve 60 for passing fluid to a cartridge, such as the cartridge 30 shown in FIG. 2. In particular, valve 60 has a longitudinal portion 64 defining an interior passage 62 communicating with port 53. Longitudinal portion 64 includes, at the distal end thereof, a tapered portion 66 terminating in an orifice 68. Tapered portion 66 is preferably inserted into the tip 34 of cartridge 30, whereby fluid passes out orifice 68 of valve 60 and into cartridge 30.

A light source 72 in the form of a light emitting diode is preferably mounted inside block 41 at side face 48. For reasons explained in greater detail hereinafter, light source 72 is oriented with respect to surface 55 to container 50 such that the incident light ray emanating from source 72 will form a 45° angle with a line normal to surface 55. Similarly, a light responsive element 74 in the form of a photo diode is preferably mounted inside block 41 at the bottom face 43. Element 74 is oriented in a predetermined path, whereby it will be impinged by a component of the incident light ray reflected from surface 55.

Figure 5:
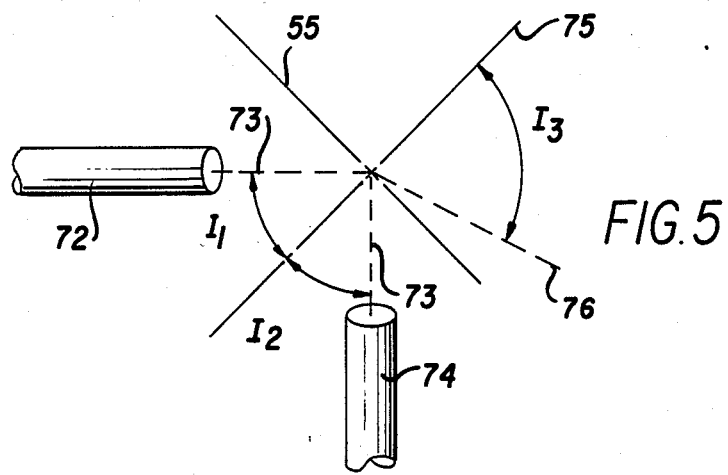
FIG. 5 is a diagrammatic representation of a portion of the device shown in FIG. 4, illustrating some of the light paths and angles helpful in understanding the invention.

The particular manner in which light is passed from source 72 and received at element 74 is shown in FIG. 5. In particular, FIG. 5 depicts a line 75 normal to surface 55 of container 50. An incident light ray 73, passed by source 72, is shown to form an angle $I_1$ with line 75, and the reflected component 75 of light ray 73 is shown to form an angle $I_2$ with line 75. Under certain circumstances a component of incident light ray 73 is refracted via a path 76 through surface 55 and into the medium (air or fluid) enclosed by container 50. Angle $I_3$ is representative of the angle formed by such a refracted ray and line 75.

The index of refraction, sometimes referenced by the letter N, is defined as the ratio of the velocity of light in a vacuum to the velocity of light in a medium. If a light ray passes from a medium with a relatively high index of refraction N, to a medium with a relatively low index of refraction N', the relationship between the angle of incidence $I_1$ and the angle of refraction $I_3$ is given by Snell's law: $\sin I_3 = N/N' \sin I_1$.

When the angle of incidence reaches a value such that $\sin I_1 = N'/N$, then $\sin I_3 = 1.0$ and $I_3 = 90°$.

At this point substantially none of the incident light is refracted through the medium of relatively low index of refraction; substantially all of the incident ray is reflected back into the medium from which it came—the medium of relatively high index of refraction. When the angle of incidence $I_1$ is of such a value that substantially all of the incident ray is reflected in the manner described, that angle is referred to as the critical angle $I_c$. This angle is represented by the equation $I_c = \arcsin N'/N$. For an acrylic/air interface, $I_c$ is about 42° (if the index for refraction for acrylic is about 1.49).

As previously explained, if $I_1$ is equal to or greater than $I_c$, substantially the entire incident ray 73 will be reflected back into the medium from which it came as a reflected component 75. Since this critical angle is about 42° for an acrylic/air interface, if source 73 is oriented at about 45° from the surface normal so that $I_1$ is greater than $I_c$, the reflected component 75 is developed, i.e., the incident ray 73 is not refracted through the container 50, but is reflected therefrom. By locating element 74 in the path of reflected component 75, the reflected component 75 can be readily detected. In accordance with conventional photo diode operation, element 74 produces a signal when impinged by light such as reflected coCmponent 75. This signal is indicative of the fact that fluid is absent from container 50.

If a liquid is present in container 50, however, the situation changes significantly. In particular, the critical angle $I_c$ for an acrylic/liquid interface is given by the equation: $I_c = \arcsin (1.33)/(1.49) = 63°$, where the index of refraction for the liquid in container 50 is about 1.33. Thus, when a liquid replaces the ambient air previously enclosed by container 50, the 45° angle of incidence $I_1$ is substantially less than the critical angle of 63°. Accordingly, substantially the entire incident ray 73 is refracted through the liquid in container 50.

In the preferred operation of the sensing device 40 shown in FIG. 4, the liquid entering container 50 may include the conjugate 19 or a chromophore and a buffer. Either of these are passed into container 50 via inlets 54, 56, respectively. Prior to the application of such fluid to container 50, light from source 72 was reflected back into the medium from which it came, causing element 74 to respond by producing a signal indicative of the absence of fluid in container 50. When sufficient fluid from inlets 54, 56 enters container 50, however, the incident ray from source 72 is refracted through the fluid rather than being reflected from the surface 55 defining the container/fluid interface. As such the required reflected component does not impinge element 74, and no signal is produced by element 74. The alternate presence and absence of a signal produced by element 74 is indicative of fluid entering a previously empty container 50. Similarly, the alternate absence and presence of that signal is indicative of the fact such fluid has been passed from container 50 via valve 60 and into cartridge 30.

Figure 7:
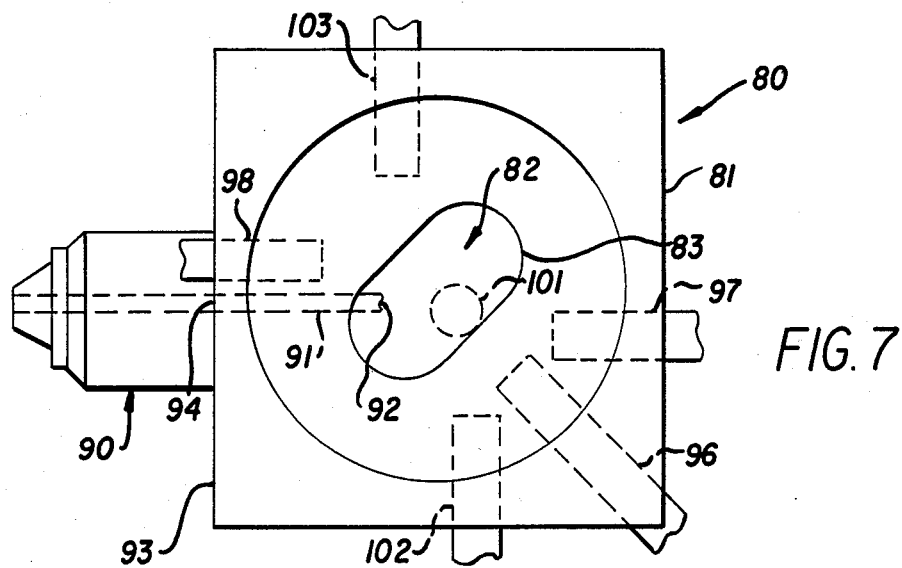
FIG. 7 is a simplified top view of the air/liquid sensing device of FIG. 6.
Figure 6:
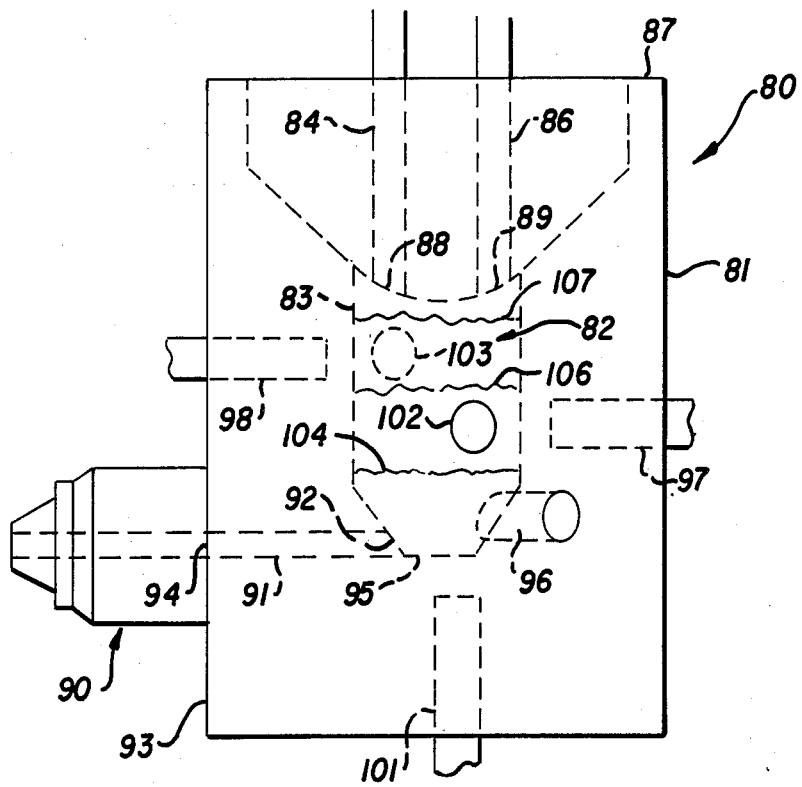
FIG. 6 is a simplified view of an air/liquid sensing device used as part of the apparatus of FIG. 3, and being representative of a second preferred embodiment of the invention.

FIGS. 6 and 7 illustrate an alternative embodiment of the invention. Specifically, these Figures illustrate an air/liquid sensing device 80 formed from block 81 of acrylic or the like. Formed inside block 81 is a cavity which serves as a container 82. Container 82 differs from container 50 in FIG. 4 in that it is preferably in the shape of an elongated column of generally elliptical cross-section (see FIG. 7). Container 82 is characterised by a surface 83 defining an interface with the space enclosed by container 82.

A pair of inlet passages 84 and 86 extends from top face 87 of the acrylic block to the top of container 82, and communicate with container 82 via inlets 88 and 89, respectively. An outlet passage 91 extends from container outlet 92 adjacent the bottom 95 of the container to a side face 93 of block 81, and terminates in a port 94 which communicates with a valve 90 for passing fluid to a cartridge (not shown).

A plurality of light sources 96, 97 and 98, preferably in the form of light emitting diodes, are mounted in cavities formed within block 81 as shown in FIGS. 6 and 7. Similarly, a plurality of light responsive elements 101, 102 and 103, preferably in the form of photodiodes, are also mounted in cavities formed within block 81.

As in the embodiment of FIGS. 4 and 5, each light source is oriented with respect to surface 83 of container 82 such that the incident light ray emanating from each source will form a 45° angle with a line normal to surface 83. Each light responsive element 101, 102 and 103 is oriented in a predetermined path whereby it will be impinged by a component of the incident light ray emanating from source 96, 97 and 98, respectively, and reflected from surface 83.

Each light source/light responsive element pair 96/101, 97/102 and 98/103 functions in the manner described above with respect to the embodiment of FIGS. 4 and 5. Thus, the incident light ray from any of sources 96, 97 or 98 will be reflected from the container when air is present in the container at the location where the incident light ray impinges the container surface 83, and can be readily detected by light responsive element 101, 102 or 103 to indicate that there is no liquid present in the container at that location.

Similarly, if a liquid is present in the container 82 at the location where any of the incident light rays impinge the container, substantially the entire incident light ray will be refracted through the liquid in the container, and no signal will be produced by the associated light responsive element.

As shown in FIGS. 6 and 7 light source 96 is positioned to impinge container 82 near the bottom 95 of the container; light source 97 is positioned to impinge container 82 approximately in the middle of the container while light source 98 is positioned to impinge the container near the top of the container.

Thus, when the container is empty, i.e., contains only air, incident light rays from all three sources will be reflected from surface 83 and received by each of the light responsive elements 101, 102 and 103. When container 82 contains liquid to a level somewhere between the positions at which light rays from sources 96 and 97 impinge the surface 83, for example, at level 104; the light ray from source 96 will be refracted from surface 83 and not received by light responsive element 101; however, light rays from sources 97 and 98 will be reflected and received by light responsive elements 102 and 103, respectively. The absence of a signal from element 101 and the presence of signals from elements 102 and 103 thus provides an indication that the level of liquid present in container 82 is above the position that the light ray from source 96 impinges the wall 83 but below the position that the light ray from source 97 impinges the wall 83 (e.g., at level 104). This information is indicative of the volume of liquid in the container.

Similarly, the absence of signals from light responsive elements 101 and 102 coupled with the presence of a signal from light responsive element 103 indicates a liquid level between the positions that light rays from sources 97 and 98 impinge wall 83, for example, at level 106.

Finally, the absence of a signal from any of the light responsive elements indicates a liquid level at or above the position where the light ray from source 98 impinges wall 83, for example, at level 107.

The embodiment of FIGS. 6 and 7, accordingly, provides an indication not only of the presence or absence of fluid in container 82, but also, an indication of the volume of fluid therein. This is an important capability when the sensing device is used in connection with the biological material analyzing apparatus of the present invention, because it permits determination not only that the proper amount of fluid has been received in container 82 to be passed to cartridge 30 via valve 90, but also that all the fluid has, in fact, been passed. This will help ensure that the analyzing apparatus will not provide a false negative due to the absence of or an insufficient amount of conjugate, for example, having been passed into cartridge 30 resulting in a failure of the chromophore to turn blue.

What has been described is a novel air/fluid sensing device particularly useful in an apparatus for analyzing a biological material. Though the embodiments described herein are preferred, other embodiments which do not depart from the true scope of the invention will be apparent to those skilled in the art. Accordingly, all such embodiments are intended to be covered by the appended claims.

I claim:

1. In an apparatus for analyzing a biological material by applying a fluid to a coated bead carried inside a cartridge, means for detecting the presence or absence of said fluid prior to its application to said cartridge comprising:
   a fluid container, communicating with said cartridge, having a surface defining an interface with the space enclosed by said container;
   a plurality of light sources each adapted to apply an incident ray to a different location on said surface of said container, said interface causing a component of said ray from each of said light sources to be reflected therefrom along a predetermined path when said fluid is absent from said container at each said location; and
   a plurality of light responsive elements, each associated with a different one of said light sources and disposed along one of said predetermined paths, each of said plurality of light responsive elements being adapted to produce a signal indicative of the absence of fluid in said container at the location where the ray from its associated light source is applied to said surface.

2. The apparatus of claim 1 wherein each of said locations is at a different height on the surface of said container.

3. The apparatus of claim 2 wherein said container is substantially in the shape of a column.

4. In an apparatus for analyzing a biological material by applying a fluid to a coated bead carried inside a cartridge, means for detecting the presence or absence of said fluid prior to its application to said cartridge comprising:
   a fluid container, communicating with said cartridge, having a surface defining an interface with the space enclosed by said container;
   a plurality of light sources each adapted to apply an incident ray to a different location on said surface of said container, said ray forming an incident angle with a line normal to said surface that is equal to or greater than the critical angle for an air/container interface, but less than the critical angle for a fluid/container interface, a component of said ray being reflected from said surface along a predetermined path when said incident angle is equal to or greater than said critical angle; and
   a plurality of light responsive elements each associated with a different one of said light sources and disposed along one of said predetermined paths and adapted to produce a signal upon receipt of said component, said signal being indicative of the absence of said fluid in said container at the location where said ray from its associated light source is applied to said surface of said containers.

5. In an apparatus for analyzing a biological material by applying a fluid to a coated bead carried inside a cartridge, means for detecting the presence or absence of said fluid prior to its application to said cartridge comprising:
   a block having a container formed therein, said container having a surface defining an interface with the space enclosed by said container;
   means, formed in said block, defining a fluid inlet communicating with said container;
   means, formed in said block, defining a fluid outlet for passing fluid from said container to said cartridge;
   a plurality of light sources each adapted to apply an incident ray to a different location on said surface of said container, said ray forming an incident angle with a line normal to said surface that is equal to or greater than the critical angle for an air/container interface, but less than the critical angle for fluid/container interface; a component of said ray being reflected from said surface along a first predetermined path when said incident angle is equal to or greater than said critical angle; and
   a plurality of light responsive elements each associated with a different one of said light sources and disposed along one of said predetermined paths and adapted to produce a signal upon receipt of said component, said signal being indicative of the absence of said fluid in said container at the location where said ray from its associated light source is applied to said surface of said container.

6. The apparatus defined in claims 4 or 5 wherein said container is substantially conically-shaped.

7. The apparatus defined in claims 4 or 5 wherein said incident angle is approximately 45°.

8. The apparatus defined in claim 7 wherein said critical angle for said air/container interface is approximately 42°.

9. The apparatus defined in claim 8 wherein said critical angle for said fluid/container interface is approximately 63°.

10. The apparatus defined in claims 1, 4 or 5 wherein said container is formed from acrylic material.

11. The apparatus of claim 5 wherein each of said locations is at a different height on the surface of said container.

12. The apparatus of claim 11 wherein said container is substantially in the shape of a column.

13. The apparatus of claim 12 wherein said container is of substantially elliptical cross-section.

14. A method for analyzing a biological material by applying a fluid to a coated bead carried inside a cartridge, a method for detecting the presence or absence of said fluid prior to its application to said cartridge comprising the steps of:

providing a container having a surface defining an interface with the space enclosed by said container;

applying a plurality of incident rays to a plurality of different locations, respectively, on said surface at an angle equal to or greater than the critical angle for an air/container interface but less than the critical angle for a fluid/container interface; and reflecting a component of each of said plurality of rays from said air/container interface, said reflected component of each of said rays being indicative of the absence of said fluid in said container at a particular location.

15. The method defined in claim 14 further includes the step of detecting said reflected component of each of said rays.

16. The method defined in claim 15 further includes the step of producing a signal upon detection of each of said reflected components.

17. The method defined in claim 16 further includes the step of passing fluid to said container.

18. The method defined in claim 17 further includes the step of refracting at least some of said plurality of rays through said fluid/container interface, whereby said reflected components are no longer detected.

19. The method defined in claim 18 further includes the step of passing said fluid from said container to said cartridge, thereby substantially emptying said container and causing said plurality rays to again be reflected from said air/container interface.

20. The method defined in claim 14 wherein each of said plurality of different locations is at a different height on said surface of said container.

* * * * *